(12) United States Patent
Izumikawa et al.

(10) Patent No.: US 10,080,713 B2
(45) Date of Patent: Sep. 25, 2018

(54) SURFACE-TREATED SPHERICAL CALCIUM CARBONATE PARTICLES FOR COSMETICS AND METHOD FOR PRODUCING SAME

(71) Applicant: SAKAI CHEMICAL INDUSTRY CO., LTD., Sakai-shi, Osaka (JP)

(72) Inventors: Hiroyuki Izumikawa, Sakai (JP); Seiji Sakamoto, Iwaki (JP); Takeshi Nishimura, Iwaki (JP)

(73) Assignee: SAKAI CHEMICAL INDUSTRY CO., LTD., Osaka (JP)

( * ) Notice: Subject to any disclaimer, the term of this patent is extended or adjusted under 35 U.S.C. 154(b) by 65 days.

(21) Appl. No.: 14/436,322

(22) PCT Filed: Oct. 16, 2013

(86) PCT No.: PCT/JP2013/078031
§ 371 (c)(1),
(2) Date: Apr. 16, 2015

(87) PCT Pub. No.: WO2014/061689
PCT Pub. Date: Apr. 24, 2014

(65) Prior Publication Data
US 2015/0290094 A1    Oct. 15, 2015

(30) Foreign Application Priority Data
Oct. 17, 2012  (JP) .................... 2012-229530

(51) Int. Cl.
| | |
|---|---|
| A61K 8/25 | (2006.01) |
| A61Q 1/12 | (2006.01) |
| A61K 8/19 | (2006.01) |
| A61K 8/891 | (2006.01) |
| A61K 8/02 | (2006.01) |
| C09C 1/02 | (2006.01) |
| C01F 11/18 | (2006.01) |

(52) U.S. Cl.
CPC ............ *A61K 8/25* (2013.01); *A61K 8/025* (2013.01); *A61K 8/0241* (2013.01); *A61K 8/19* (2013.01); *A61K 8/891* (2013.01); *A61Q 1/12* (2013.01); *C01F 11/18* (2013.01); *C09C 1/024* (2013.01); *A61K 2800/412* (2013.01); *A61K 2800/621* (2013.01); *A61K 2800/63* (2013.01); *A61K 2800/651* (2013.01); *A61K 2800/654* (2013.01); *C01P 2004/32* (2013.01); *C01P 2004/61* (2013.01); *C01P 2004/62* (2013.01)

(58) Field of Classification Search
None
See application file for complete search history.

(56) References Cited

U.S. PATENT DOCUMENTS

| | | | |
|---|---|---|---|
| 6,534,044 B1 | 3/2003 | Wada et al. | |
| 2005/0235872 A1* | 10/2005 | Tanabe | C01F 11/181 106/463 |
| 2008/0305338 A1 | 12/2008 | Mizutani et al. | |
| 2010/0015189 A1* | 1/2010 | Perron | A61K 8/044 424/401 |
| 2010/0098780 A1* | 4/2010 | Ono | A61Q 1/02 424/683 |

FOREIGN PATENT DOCUMENTS

| | | |
|---|---|---|
| JP | 55-95617 | 7/1980 |
| JP | 4-238812 | 8/1992 |
| JP | 2006-206496 | 8/2006 |
| JP | 2012-088462 | 5/2012 |
| JP | 2012-240930 | 12/2012 |
| WO | 00/042112 | 7/2000 |
| WO | 2007/039953 | 4/2007 |
| WO | WO-2007-039953 | * 4/2007 |
| WO | WO-2007-039953 | * 12/2007 |
| WO | 2010/146630 | 12/2010 |
| WO | WO-2010-146630 | * 12/2010 |

OTHER PUBLICATIONS

International Search Report, dated Jan. 21, 2014; PCT/JP2013/078031 (2 pages—submitted on Apr. 16, 2015).
Takumi Tanaka: "The development and properties of cerium oxide as a novel UV filter and cosmetics application"; Fragrance Journal, Oct. 2008, vol. 36, No. 10, pp. 65-69 (English Abstract/International Search Report).

* cited by examiner

*Primary Examiner* — Celeste A Roney
(74) *Attorney, Agent, or Firm* — Hamre, Schumann, Mueller & Larson, P.C.

(57) ABSTRACT

The invention provides surface-treated spherical calcium carbonate particles for use in cosmetics which comprise spherical calcium carbonate particles having a volume mean diameter in a range of 0.5 to 20 μm, and having on their surfaces a hydrous silica coating, and further a silicone oil coating on the hydrous silica coating. The surface-treated spherical calcium carbonate particles for use in cosmetics are obtained by forming a hydrous silica coating on the surfaces of spherical calcium carbonate particles, and then by forming a silicone oil coating on the surfaces of the hydrous silica coating of the particles.

10 Claims, No Drawings

SURFACE-TREATED SPHERICAL CALCIUM CARBONATE PARTICLES FOR COSMETICS AND METHOD FOR PRODUCING SAME

FIELD OF THE INVENTION

The present invention relates to surface-treated spherical calcium carbonate particles for use in cosmetics, and a method for producing the same. The invention particularly relates to surface-treated spherical calcium carbonate particles which are superior in water repellency and slipperiness, and are such that when they are incorporated in cosmetics and the resulting cosmetics are applied to the skin, the cosmetics are superior in spreadability and in feel, and in addition, they cause no smearing of makeup with perspiration.

The invention further relates to a method for producing the surface-treated spherical calcium carbonate particles for use in cosmetics.

BACKGROUND ART

It has hitherto been proposed to use various inorganic particles as a material combined with cosmetics for improving their spreadability. Spherical calcium carbonate is one of them. The spherical calcium carbonate itself, however, has poor stability in water, and thus it has been proposed that the spherical calcium carbonate is surface-treated with a higher fatty acid such as stearic acid (see Patent Literature 1).

In particular, in the case of cosmetics such as foundation makeup, it is strongly required for inorganic particles combined therewith to be superior in water repellency in order to prevent makeup from smearing with perspiration. However, even if the spherical calcium carbonate is surface-treated with a higher fatty acid or a salt thereof as described above, it is not sufficient in water repellency, and it is not sufficient in feel, either.

Then, for example, a method is proposed in which (extender) pigment particles including calcium carbonate are coated with organopolysiloxane such as organohydrogen polysiloxane or diorganopolysiloxane to obtain a surface-treated (extender) pigment for use in cosmetics (see Patent Literature 2).

According to the method described above, however, the organopolysiloxane is emulsified with a surfactant, a(n) (extender) pigment is mixed with the resulting emulsion, and the mixture is heated, dried, and crushed to obtain a surface-treated (extender) pigment for use in cosmetics. Thus, the method has many production steps and is complicated, and moreover, when calcium carbonate is used as the pigment, it is difficult to directly form an organopolysiloxane coating in an effective amount on the surfaces of the calcium carbonate particles. Furthermore, the water repellency and slipperiness of surface-treated (extender) pigment for use in cosmetics have not been quantitatively evaluated. They have been only insufficiently studied.

PRIOR ART LITERATURES

Patent Literatures

Patent Literature 1: JP 55-95617A
Patent Literature 2: JP 2006-206496A

SUMMARY OF INVENTION

Technical Problem

It is an object of the invention to solve the problems involved in the conventional surface-treated spherical calcium carbonate particles for use in cosmetics as described above, and to provide surface-treated spherical calcium carbonate particles for use in cosmetics which are superior in water repellency and slipperiness, and are such that when they are incorporated in cosmetics and the resulting cosmetics are applied to the skin, the cosmetics are superior in spreadability and in feel, and in addition, they cause no smearing of makeup with perspiration.

It is a further object of the invention to provide a method for producing the surface-treated spherical calcium carbonate particles for use in cosmetics as described above.

Solution to Problem

The invention provides surface-treated spherical calcium carbonate particles for use in cosmetics which comprise spherical calcium carbonate particles having a volume mean diameter in a range of 0.5 to 20 µm, and having on their surfaces a hydrous silica coating, and further a silicone oil coating on the hydrous silica coating.

The invention also provides a method for producing the surface-treated spherical calcium carbonate particles for use in cosmetics comprising the steps of:

adding an aqueous solution of an alkali metal silicate to an aqueous dispersion of spherical calcium carbonate particles having a volume median diameter in a range of 0.5 to 20 µm;

adding an acid to the aqueous dispersion to adjust the pH thereof to a range of 5.0 to 9.0, thereby separating the product obtained, washing and drying the product to obtain spherical calcium carbonate particles having on their surfaces a hydrous silica coating;

kneading the spherical calcium carbonate particles having on their surfaces the hydrous silica coating with a silicone oil together with a volatile organic solvent to obtain a kneaded product;

heating the kneaded product to dry and remove the volatile organic solvent therefrom, thereby forming a silicone oil coating on the hydrous silica coating of the spherical calcium carbonate particles.

The invention further provides the surface-treated spherical calcium carbonate particles for cosmetics obtained by the method described above, and cosmetics comprising the surface-treated spherical calcium carbonate particles for cosmetics obtained by the method described above.

Advantageous Effects of Invention

Because the surface-treated spherical calcium carbonate particles for use in cosmetics of the invention have an effective amount of silicone oil coating on their surfaces, they are superior not only in water repellency but also in slipperiness. When the cosmetics containing such surface-treated spherical calcium carbonate particles therein are applied to the skin, they are superior in spreadability and in feel, and further they causes no smearing of makeup with perspiration.

According to the method for producing the surface-treated spherical calcium carbonate particles for use in cosmetics of the invention, as an effective amount of hydrous silica coating is formed on the surfaces of the spherical calcium carbonate particles, and then a silicone oil coating is formed on the hydrous silica coating, an effective amount of silicone oil coating can be provided with the surfaces of the spherical calcium carbonate particles. Consequently, the obtained surface-treated spherical calcium carbonate particles for use in cosmetics are superior not only in water repellency but also in slipperiness. When the cosmetics containing such surface-treated spherical calcium carbonate particles for use therein are applied to the skin, they are superior in spreadability and in feel, and moreover, they causes no smearing of makeup with perspiration.

DESCRIPTION OF EMBODIMENTS

The surface-treated spherical calcium carbonate particles for use in cosmetics of the invention are spherical calcium carbonate particles having a volume median diameter in a range of 0.5-20 µm, and having on their surfaces a hydrous silica coating, and further a silicone oil coating on the hydrous silica coating.

The surface-treated spherical calcium carbonate particles for use in cosmetics of the invention are obtained by:

adding an aqueous solution of an alkali metal silicate to an aqueous dispersion of spherical calcium carbonate particles having a volume median diameter in a range of 0.5 to 20 µm;

adding an acid to the aqueous dispersion to adjust the pH thereof to a range of 5.0 to 9.0, thereby separating the product obtained, washing and drying the product to obtain spherical calcium carbonate particles having on their surfaces a hydrous silica coating;

kneading the spherical calcium carbonate particles having on their surfaces the hydrous silica coating with a silicone oil together with a volatile organic solvent to obtain a kneaded product;

heating the kneaded product to dry and remove the volatile organic solvent therefrom, thereby forming a silicone oil coating on the hydrous silica coating of the spherical calcium carbonate particles.

The method for producing the surface-treated spherical calcium carbonate particles for use in cosmetics of the invention is first described.

It is necessary in the invention that the spherical calcium carbonate used as a raw material has a volume median diameter in a range of 0.5-20 µm so that the resulting surface-treated spherical calcium carbonate particles are superior in feel and slipperiness when they are incorporated in cosmetics.

When the spherical calcium carbonate particles used have a volume median diameter of larger than 20 µm, they are felt as foreign substances on the skin when they are combined with cosmetics. On the other hand, when they have a volume median diameter of smaller than 0.5 µm, they have insufficient slipperiness. Thus, even if such spherical calcium carbonate particles are provided thereon with a hydrous silica coating and a silicone oil coating, and incorporated in cosmetics, the resulting cosmetics are inferior in feel when applied to the skin, and cause makeup to run.

In particular, the spherical calcium carbonate particles used as a raw material have preferably a volume median diameter in a range of 1-10 µm, and most preferably in a range of 1.5-7.5 µm.

Furthermore, it is enough that the spherical calcium carbonate particles used in the method of the invention have a sphericity, defined by the ratio of minor axis/major axis, of 0.80 or more.

The spherical calcium carbonate particles described above can be produced preferably by a method described in Japanese Patent No. 3013445. The spherical calcium carbonate particles obtained by the method described in the patent have a volume median diameter of about several µm to about 10 µm, and contain vaterite crystals in a content of 90% or more, preferably about 99%, which are spherical calcium carbonate particles preferably used in the invention.

The content of the vaterite crystals in the calcium carbonate can be obtained according to the following formula (1), as already well known (M. S. Rao, Bull. Chem. Soc. Japan, 46, 1414 (1973)).

The content of vaterite crystals $F(v)=f(v)\times 100$    (1)

wherein $$f(v)=1-I_{104(c)}/(I_{110(v)}+I_{112(v)}+I_{114(v)}+I_{104(c)})$$

in which $I_{104(c)}$ is an X-ray diffraction intensity on the 104 face of calcite, $I_{110(v)}$ is an X-ray diffraction intensity on the 110 face of vaterite, $I_{112(v)}$ is an X-ray diffraction intensity on the 112 face of vaterite, and $I_{114(v)}$ is an X-ray diffraction intensity on the 114 face of vaterite.

According to the method described in the above-mentioned patent, calcium chloride and a hydrogen carbonate and/or a carbonate are reacted in water in the presence of a certain kind of phosphorus acid compound in an amount of 0.3% by weight or more relative to the theoretical yield of calcium carbonate formed, thereby to obtain spherical calcium carbonate particles containing 90% or more of vaterite crystals of calcium carbonate.

In the above-mentioned method, various kinds of phosphoric acid compounds can be used. Typical examples include sodium trimetaphosphate, sodium hexametaphosphate, sodium tripolyphosphate, 1-hydroxyethylidene-1,1-diphosphonic acid, aminotri(methylenephosphonic acid), ethylenediaminetetra(methylenephosphonic acid), sodium bis(poly-2-carboxyethyl)phosphinate, methyl acid phosphate,butyl acid phosphate, 2-phosphonobutanetricarboxylic acid-1,2,4, etc.

According to the method of the invention, the spherical calcium carbonate particles having a hydrous silica coating in an effective amount on their surfaces are obtained by dispersing spherical calcium carbonate particles in water to prepare an aqueous dispersion, adding an aqueous solution of an alkali metal silicate such as sodium silicate to the aqueous dispersion at room temperature, adding an acid to the aqueous dispersion to neutralize the aqueous dispersion to a pH in a range of 5.0 to 9.0 thereby to deposit hydrous silica on the surfaces of the spherical calcium carbonate particles, and separating the resulting product from the dispersion and drying it.

Further according to the invention, the spherical calcium carbonate particles having a hydrous silica coating in an effective amount on their surfaces are obtained usually by using an alkali metal silicate in an amount of 0.1 to 10 parts by weight in terms of silica ($SiO_2$) per 100 parts by weight of spherical calcium carbonate particles when a hydrous silica coating is formed on the surfaces of the spherical calcium carbonate particles, thereby to form a hydrous silica coating in an amount of 0.1 to 10 parts by weight in terms of silica ($SiO_2$) per 100 parts by weight of spherical calcium carbonate particles, although the method is not limited to the above.

According to the invention, in particular, it is preferred that an alkali metal silicate is used in an amount of 1.0 to 5.0 parts by weight in terms of silica ($SiO_2$) per 100 parts by weight of spherical calcium carbonate particles thereby to form a hydrous silica coating in an amount of 1.0 to 5.0 parts by weight in terms of silica ($SiO_2$) per 100 parts by weight of spherical calcium carbonate particles.

In the method of the invention, the alkali metal silicate used is almost quantitatively forms a hydrous silica coating on the surfaces of the spherical calcium carbonate particles. Thus, it can be said that the amount of the alkali metal silicate used in terms of silica equals to the amount of hydrous silica coating formed on the surfaces of the spherical calcium carbonate particles. In the invention, accordingly, all the amount of hydrous silica coating per 100 parts by weight of spherical calcium carbonate particles is expressed as the amount of alkali metal silicate used in terms of silica ($SiO_2$) per 100 parts by weight of the spherical calcium carbonate particles used.

When the amount of the hydrous silica coating is less than 0.1 parts by weight per 100 parts by weight of the spherical calcium carbonate particles in terms of silica ($SiO_2$), even if the spherical calcium carbonate particles are surface-treated with a silicone oil, it is difficult to adapt the silicone oil to the spherical calcium carbonate particles, and it is feared that the spherical calcium carbonate particles cannot be provided with an effective amount of a silicone oil coating. On the other hand, when the amount of the hydrous silica coating is more than 10 parts by weight per 100 parts by weight of the spherical calcium carbonate particles in terms of silica ($SiO_2$), the spherical calcium carbonate particles have a thick hydrous silica coating on the surfaces which are originally excellent in light diffusibility, and it is feared that a soft focusing effect, i.e., an effect for making the skin look highly transparent and blurred when the particles are combined with cosmetics and it is applied to the skin, is deteriorated.

When the hydrous silica coating is formed on the surfaces of spherical calcium carbonate particles, the aqueous dispersion of the spherical calcium carbonate particles contain the spherical calcium carbonate particles preferably in a range of 10 to 1000 g/L, although not limited. The aqueous solution of alkali metal silicate contains the alkali metal silicate preferably in a range of 1.0 to 1000 g/L in terms of silica ($SiO_2$), although not limited.

An inorganic acid is usually used preferably as an acid to neutralize the alkali metal silicate, and, for example, sulfuric acid or hydrochloric acid is used. It is preferred that the acid is added slowly to the dispersion with stirring so that the aqueous dispersion of the spherical calcium carbonate particles comes gradually to have a pH in a range of 5.0 to 9.0, preferably a pH in a range of 6.5 to 7.5, most preferably a pH of almost 7.0.

In this way, an acid is added to the aqueous dispersion of the spherical calcium carbonate particles containing the alkali metal silicate to neutralize the dispersion, and then, while continuing stirring, the resulting aqueous dispersion is aged for from one hour to several hours so that a hydrous silica coating is formed on the surfaces of the spherical calcium carbonate particles.

Thereafter, the aqueous dispersion of the spherical calcium carbonate particles having on the surfaces a hydrous silica coating is filtered to separate the spherical calcium carbonate particles having on the surface a hydrous silica coating from the aqueous dispersion. The spherical calcium carbonate particles are washed with water, and are dried by heating at a temperature in a range of 100 to 110° C. thereby to obtain the spherical calcium carbonate particles having a hydrous silica coating thereon as dry powder.

Then, the spherical calcium carbonate particles having on the surface a hydrous silica coating thus obtained are treated with a silicone oil to provide the spherical calcium carbonate particles having on the surfaces a hydrous silica coating and an effective amount of a silicone oil coating on the hydrous silica coating.

In the invention, the surface-treated spherical calcium carbonate particles having thereon an effective amount of a silicone oil coating refers to surface-treated spherical calcium carbonate particles which are superior in water repellency and slipperiness, and are such that when they are incorporated in cosmetics and the resulting cosmetics are applied to the skin, the cosmetics are superior in spreadability and in feel.

The spherical calcium carbonate particles having thereon an effective amount of a hydrous silica coating refers to spherical calcium carbonate particles which exhibit an excellent water repellency and slipperiness when they have been treated with a silicone oil so that when the resulting surface-treated spherical calcium carbonate particles are combined with cosmetics and the cosmetic are applied to the skin, they exhibit superior spreadability and feel when they are applied to the skin, as described hereinbefore.

More specifically, in order to treat the spherical calcium carbonate particles having thereon a hydrous silica coating with a silicone oil, by way of examples, a powder of the spherical calcium carbonate particles having thereon a hydrous silica coating is first mixed with an appropriate volatile organic solvent to prepare a kneaded product of the spherical calcium carbonate particles having thereon a hydrous silica coating so that the particles are easily adapted to a silicone oil. The kneaded product is then mixed and further kneaded with a silicone oil to prepare an evenly kneaded product. The kneaded product is then heated at a temperature in a range of 110 to 150° C. to remove the organic solvent therefrom. In this manner, there are obtained the surface-treated spherical calcium carbonate particles having on the surfaces a hydrous silica coating and a silicone oil coating on the hydrous silica coating as powder.

Although the volatile organic solvent used in the invention is not particularly limited to specific ones so far as it is easily adapted to a silicone oil, and it readily evaporates when the kneaded product thereof with the spherical calcium carbonate particles having on the surface a hydrous silica coating is heated and dried, an aliphatic lower alcohol of 1 to 4 carbon atoms such as isopropyl alcohol is preferably used. The amount of the volatile organic solvent used is also not specifically limited so far as the amount is enough to form a kneaded product thereof with the spherical calcium carbonate particles having on the surface a hydrous silica coating, and the amount is usually in a range of about 30 to 700 mL in relation to 100 g of the spherical calcium carbonate particles having on the surfaces a hydrous silica coating.

The surface-treated spherical calcium carbonate particles for use in cosmetics having thereon an effective amount of a silicone oil coating are obtained by forming a hydrous silica coating on the spherical calcium carbonate particles, and then by forming a silicone oil coating in an amount of 0.1 to 10 parts by weight, preferably in an amount of 1.0 to 8.0 parts by weight in relation to 100 parts by weight of the spherical calcium carbonate particles having on the surfaces the hydrous silica coating by using a silicone oil in an amount of 0.1 to 10 parts by weight, preferably in an amount of 1.0 to 8.0 parts by weight in relation to 100 parts by weight of the spherical calcium carbonate particles having on the surfaces the hydrous silica coating.

When the amount of silicone oil coating is less than 0.1 parts by weight per 100 parts by weight of the spherical calcium carbonate particles, there is a fear that the resulting surface-treated spherical calcium carbonate particles fail to have sufficient water repellency. On the other hand, when the amount of silicone oil coating is more than 10 parts by weight per 100 parts by weight of the spherical calcium carbonate particles, there is a fear that the resulting surface-treated spherical calcium carbonate particles are remarkably deteriorated in feel.

According to the invention, as the silicone oil used forms substantially quantitatively a silicone oil coating on the hydrous silica coating on the spherical calcium carbonate particles, it can be said that all the amount of the silicone oil used forms a silicone oil coating on the hydrous silica coating on the surface of the spherical calcium carbonate particles. Therefore, in the invention, the amount of the silicone coating per 100 parts by weight of the spherical calcium carbonate particles having thereon the hydrous silica coating is represented by the amount of the silicone oil used per 100 parts by weight of the spherical calcium carbonate particles having thereon the hydrous silica coating.

The silicone oil used in the invention is not particularly limited, and oil which is used as a hydrophobing agent is preferable. Typical examples thereof may include methicone, hydrogen dimethicone, dimethicone (dimethyl polysiloxane), highly polymerized dimethicone (highly polymerized dimethyl polysiloxane), cyclomethicone (cyclic dimethyl siloxane, decamethyl cyclopentasiloxane), methyl trimethicone, perfluoroalkyl trialkoxysilane, phenyl trimethicone, diphenyl dimethicone, phenyl dimethicone, stearoxypropyl dimethylamine, (aminoetliylaminopropyl methicone/dimethicone) copolymers, dimethiconol, dimethiconol crosspolymers, silicone resins, silicone rubber, amino-modified silicone such as aminopropyl dimethicone, amodimethicone, and the like, cation-modified silicone, polyether-modified silicone such as dimethicone copolyol, polyglycerin-modified silicone, sugar-modified silicone, carboxylic acid-modified silicone, phosphoric acid-modified silicone, sulfuric acid-modified silicone, alkyl-modified silicone, fatty acid-modified silicone, alkyl ether-modified silicone, amino acid-modified silicone, peptide-modified silicone, fluorine-modified silicone, cation-modified and polyether-modified silicone, amino-modified and polyether-modified silicone, alkyl-modified and polyether-modified silicone, trialkoxysilyl-modified organopolysiloxane such as triethoxysilylethyl polydimethylsiloxyethylhexyl dimethicone, trialkoxysilyl-modified silicone branched organopolysiloxane, polysiloxane-oxyalkylene copolymers, and the like.

According to the invention, an effective amount of silicone oil coating is evenly formed on the surfaces of the spherical calcium carbonate particles by forming a hydrous silica coating on the surfaces of the spherical calcium carbonate particles having a volume median diameter in a range of 0.5-20 μm, and then by forming a silicone oil coating on the hydrous silica coating of the spherical calcium carbonate particles. The surface-treated spherical calcium carbonate particles obtained in this way are superior in water repellency but also in slipperiness, and consequently, they are such that when they are incorporated in cosmetics and the resulting cosmetics are applied to the skin, the cosmetics are superior in spreadability and in feel, and in addition, they do not cause makeup to run with perspiration.

The surface-treated spherical calcium carbonate particles for cosmetics of the invention, accordingly, have a mean coefficient of frictional of 0.70 or less and a water repellency defined by an amount of isopropyl alcohol of 40 mL or more. Thus, when such surface-treated spherical calcium carbonate particles of the invention are incorporated in cosmetics, there are obtained cosmetics which are not only superior in feel when they are applied to the skin, but also cause no smearing of makeup with perspiration.

The cosmetics of the invention contain the surface-treated spherical calcium carbonate particles of the invention, and they can be incorporated in cosmetics in a usual manner. The surface-treated spherical calcium carbonate particles of the invention are incorporated in cosmetics in an amount in a range of usually 0.1 to 95% by weight, preferably 5 to 50% by weight, though depending on the kind of the cosmetics.

In addition to the surface-treated spherical calcium carbonate particles of the invention as described above, the cosmetics of the invention may contain various kinds of raw materials or compounds usually used in cosmetics so far as they do not affect the desirable effects of the cosmetics of the invention. Such raw materials or compounds include, for example, powders such as a white pigment, a colored pigment, and an extender pigment, general use oil agents such as solid oil, semisolid oil, and liquid oil, fluorine containing oil agent, silicone oil, silicone gum, silicone resin, a surfactant, an antioxidant, ultraviolet rays absorbent, a water soluble polymer, cosmetic components, water, fragrance and so on.

The cosmetics of the invention are not particularly limited, and may include, for example, skin care cosmetics such as lotion, emulsion, and cream; and makeup cosmetics such as powdery foundation makeups, oily foundation cream, water-in-oil type foundation makeups, face powder, rouge, base cream, suntan lotion, eyeliner, eyeshadow, eyebrow, mascara, lipsticks, and lip cream. They may be produced in a usual manner.

EXAMPLES

The invention is in more detail described with reference to examples and comparative examples given below, but the invention is not limited at all by those examples. In the following examples and comparative examples, the volume median diameter of spherical calcium carbonate particles and the electric conductivity of filtrates were measured as follows. The sphericity, water repellency and slipperiness as properties of spherical calcium carbonate particles were measured as follows.

Volume Median Diameter of Spherical Calcium Carbonate Particles:

The volume median diameter D50 was measured using a laser diffraction/dispersion particle size distribution measuring equipment LA-750 manufactured by Horiba, Ltd.

Electric Conductivity of Filtrate:

The measurement was carried out by using an electric conductivity measuring equipment ES-12 manufactured by Horiba, Ltd.

Sphericity of Surface-Treated Spherical Calcium Carbonate Particles 100 particles were randomly selected in SEM photographs, and a major axis and a minor axis of each particle were measured. A ratio of the minor axis/the major axis was obtained, which was determined as sphericity.

Water Repellency of Surface-Treated Spherical Calcium Carbonate Particles 300 mL of deionized water was put to a 500 mL capacity beaker. Into the beaker was put 1 g of a sample, i.e., a surface-treated spherical calcium carbonate powder, while the deionized water was stirred at a stirring speed of 250 rpm, and then the mixture was stirred for further one minute at the same stirring speed as above. After the stirring was stopped, turbidity of the deionized water in the beaker was visually observed. A case where there was no precipitation or turbidity was rated as "good," and a case where there was precipitation or turbidity even a little was rated as "poor."

When the test result was "good," the test was performed in an alcohol/water mixture composed of 5 mL of isopropyl alcohol and 295 mL of deionized water in the same manner as above. Hereinafter, the test was repeated in a manner in which the amount of the isopropyl alcohol was increased 5 mL by 5 mL and the amount of the deionized water was decreased 5 mL by 5 mL so that the amount of the mixture was 300 mL until the test result was "poor." An amount of the isopropyl alcohol when the test result was finally "poor" was determined as an index of water repellency. The larger the amount of the isopropyl alcohol when the test result was finally "poor," the more excellent the water-repellency of the sample, i.e., the surface-treated spherical calcium carbonate powder.

Slipperiness of Surface-Treated Spherical Calcium Carbonate Particles

A double-sided adhesive tape having a width of 25 mm was pasted on a sheet of slide glass. About 0.5 g of surface-treated spherical calcium carbonate particles was put and spread on the double-sided adhesive tape with a cosmetic puff. Then, the coefficient of friction of the surface-treated spherical calcium carbonate particles spread on the double-sided tape was measured using a friction tester KES-SE (manufactured by Kato Tech Co., Ltd.) together with a silicone rubber friction block. The mean coefficient of friction and the deviation of coefficient of friction were calculated based on the mean value of the frictional coefficients ($\mu$) in a length of 20 mm. Thus, the slipperiness of the particles were evaluated.

1. Production of Surface-Treated Spherical Calcium Carbonate Particles

Example 1

(Production of Spherical Calcium Carbonate)

9.8 g of calcium chloride dihydrate were put in a 1-L capacity beaker, and was dissolved in ion exchanged water, to prepare 200 mL of aqueous solution. In addition, 35 g of sodium carbonate was dissolved in ion exchanged water to prepare 200 mL of aqueous solution. Further, 0.05 g of sodium hexametaphosphate were dissolved in ion exchanged water to prepare 10 mL of aqueous solution.

While the aqueous solution of calcium chloride was stirred with a magnetic stirrer at room temperature, the whole amount of the aqueous solution of sodium carbonate was added to the aqueous solution of calcium chloride, followed by stirring for 10 minutes. The whole amount of the aqueous solution of sodium hexametaphosphate was then added to the resulting mixture, followed by stirring for 30 minutes.

The calcium carbonate obtained in this way was filtered, and washed repeatedly until the filtrate came to have an electric conductivity of 70 μS/cm or less, and then it was stood in a box dryer at a temperature of 105° C. and dried. After 12 hours, the calcium carbonate was taken out of the dryer and cooled, to provide spherical calcium carbonate particles. The spherical calcium carbonate particles thus obtained were found to have a volume median diameter of 4.0 μm, a sphericity of 0.91, and a content of 99% of vaterite crystals.

(Hydrous Silica Coating of Spherical Calcium Carbonate Particles)

500 g of the spherical calcium carbonate particles were dispersed in 3-L of pure water in a 10-L capacity stainless steel container provided with a stirrer, and stirred for 10 minutes at normal temperature to prepare an aqueous dispersion of the spherical calcium carbonate particles.

150 mL of aqueous solution of sodium silicate ($Na_2SiO_3$) having a 100 g/L concentration in terms of silica ($SiO_2$) was added dropwise at a rate of 10 mL per minute to the dispersion while it was stirred, and then the resulting mixture was stirred for 30 minutes.

Then, 1.5% by weight concentration sulfuric acid was added dropwise to the dispersion at a rate of 4 to 8 mL per minute with stirring over a period of 90 minutes while the pH of the dispersion was monitored to put the dispersion at a pH of 7.0, followed by aging for one hour with continued stirring.

The dispersion of the thus treated spherical calcium carbonate particles was filtered with 5C filter paper, and the obtained spherical calcium carbonate particles were washed with water until the filtrate came to have an electric conductivity of 100 μS/cm. Then, the obtained spherical calcium carbonate particles were dried in a box dryer at a temperature of 105° C. for 12 hours. The spherical calcium carbonate particles were then taken out of the dryer, and cooled, to provide powder of spherical calcium carbonate particles having a hydrous silica coating on the surfaces in an amount of 3 parts by weight per 100 parts by weight of the spherical calcium carbonate particles.

(Treatment of Spherical Calcium Carbonate Particles Having Thereon a Hydrous Silica Coating with a Silicone Oil)

50 g of the powder of spherical calcium carbonate particles having the hydrous silica coating on the surfaces, and then 30 mL of isopropyl alcohol, were put in a polyethylene bag. While the bag was rubbed by hands, isopropyl alcohol was further added to the mixture little by little, to prepare a kneaded product.

1.5 g of hydrogen dimethicone KF-9901 (produced by Shin-Etsu Chemical Co., Ltd.) was added to the kneaded product in the bag, and the bag was rubbed in the same manner as above by hands so that the spherical calcium carbonate particles having the hydrous silica coating on the surfaces were fully adapted to the hydrogen methicone. The content was taken out of the bag and placed on a flat dish on which aluminum foil had been spread, heated and dried at a temperature of 140° C. for 12 hours in a dryer, and allowed to cool to room temperature, thereby to provide powder of surface-treated spherical calcium carbonate particles having the hydrous silica coating on the surfaces and a silicone coating thereon in an amount of 3 parts by weight per 100 parts by weight of the spherical calcium carbonate particles having the hydrous silica coating on the surfaces.

Example 2

In place of 1.5 g of hydrogen dimethicone KF-9901, 1.5 g of triethoxysilylethyl polydimethylsiloxyethylhexyl dimethicone KF-9909 (produced by Shin-Etsu Chemical Co., Ltd.) was used, and the otherwise in the same manner as in Example 1, the spherical calcium carbonate particles having the hydrous silica coating on the surfaces were treated with the silicone oil.

Comparative Example 1

Without coating the spherical calcium carbonate particles with hydrous silica on the surfaces, they are treated with the silicone oil in the same manner as in Example 1 thereby to provide surface-treated spherical calcium carbonate particles as a comparative example.

Comparative Example 2

In place of 1.5 g of hydrogen dimethicone KF-9901, 1.5 g of bis(3-[triethoxysilyl]propyl)tetrasulfon Si69 (produced by Degussa AG Corporation), that is, a silane coupling agent, was used, and the spherical calcium carbonate particles having the hydrous silica coating on the surfaces were treated in the same manner as in Example 1, to provide surface-treated spherical calcium carbonate particles as a comparative example.

Comparative Example 3

100 g of the spherical calcium carbonate particles obtained in Example 1 and 1-L of ion exchanged water were put in a 3-L capacity beaker provided with a stirrer, and they were stirred at a temperature of 30° C. for 10 minutes at a stirring speed of 200 rpm, to disperse the spherical calcium carbonate particles in the ion exchanged water to prepare an aqueous dispersion. 3.5 g of sodium myristate was dissolved in 1.2-L of ion exchanged water to prepare an aqueous solution.

The whole amount of the aqueous solution of sodium myristate was added dropwise to the aqueous dispersion of the spherical calcium carbonate particles at a rate of 20 mL per minute. After the dropwise addition, the temperature of the resulting mixture was raised to 70° C., and then aged for 30 minutes. Then, the resulting mixture was cooled to room temperature, and sulfuric acid having a concentration of 130 g/L was added to the mixture little by little to put the mixture at a pH of 7.0.

The aqueous slurry of surface-treated spherical calcium carbonate particles obtained in this way was filtered with 5C filter paper 110 cm in diameter. The spherical calcium carbonate particles were washed repeatedly with deionized water until the filtrate came to have an electric conductivity of 50 μS/cm or less. After washing, the resulting surface-treated spherical calcium carbonate particles were dried in a box dryer at a temperature of 105° C. After 12 hours, the calcium carbonate particles were taken out of the dryer and cooled, to provide surface-treated spherical calcium carbonate particles as a comparative example.

The mean coefficient of friction, the mean deviation of the coefficient of friction and water repellency of the surface-treated spherical calcium carbonate particles obtained in the above-mentioned Examples and Comparative Examples are shown in Table 1.

TABLE 1

| | Examples | | Comparative Examples | | |
|---|---|---|---|---|---|
| | 1 | 2 | 1 | 2 | 3 |
| Mean Coefficient of Friction | 0.66 | 0.66 | 0.62 | 0.64 | 0.63 |
| Mean Deviation of Coefficient of Friction | 0.0088 | 0.0103 | 0.0092 | 0.009 | 0.0083 |
| Amount (mL) of Isopropyl Alcohol When the Mixture Became Turbid | 50 | 60 | 0 | 30 | 30 |

The surface-treated spherical calcium carbonate particles for use in cosmetics according to the invention has an isopropyl alcohol quantity of 40 mL or more as an index that the invention prescribes for water repellency. Thus, they are superior in water repellency, and have a mean coefficient of friction of 0.70 or less, showing that they are superior in slipperiness.

As clear when Examples 1 and 2 are compared with Comparative Example 1, there are obtained spherical calcium carbonate particles superior in water repellency by coating spherical calcium carbonate particles with hydrous silica, and then with a silicone oil.

As clear when Examples 1 and 2 are compared with Comparative Example 2, if spherical calcium carbonate particles are first coated with hydrous silica and then with a silane coupling agent, the thus treated spherical calcium carbonate particles have still an insufficient water repellency.

Furthermore, as clear when Examples 1 and 2 are compared with Comparative Example 3, even if spherical calcium carbonate particle are treated with a fatty acid, they are still insufficient in water repellency.

Production of Cosmetics

Examples 3, 4, and Comparative Examples 4 to 6

Each of the formulations shown in Table 2 was put in a 75 mL-capacity glass vessel, and it was then mixed using Labo Mill Surplus (manufactured by AS ONE Corporation) for one minute. The obtained mixed powder was put on a metal dish, which was subjected to compression molding with a pressure of 40 kg/cm² for 3 minutes to provide a powdery foundation makeup of Examples and Comparative Examples, respectively.

Evaluation of Feel

Fifteen panelists evaluated the feel, i.e., either pleasant texture or unpleasant texture, of the powdery foundation makeups obtained in Examples and Comparative Examples. Evaluation criteria are as shown below, and the results are shown in Table 2.

AA: 13 or more panelists felt a good feel.
A: 9 to 12 panelists felt a good feel.
B: 5 to 8 panelists felt a good feel.
C: 4 or less panelists felt a good feel.

TABLE 2

| | Examples | | Comparative Examples | | |
|---|---|---|---|---|---|
| Components (g) | 3 | 4 | 4 | 5 | 6 |
| Sericite | 15 | 15 | 15 | 15 | 15 |
| Talc | 15 | 15 | 15 | 15 | 15 |
| Flake-shaped Barium Sulfate | 15 | 15 | 15 | 15 | 15 |
| (Red) Iron Oxide | 1 | 1 | 1 | 1 | 1 |
| Magnesium Myristate | 3 | 3 | 3 | 3 | 3 |
| Squalane | 6 | 6 | 6 | 6 | 6 |
| Isopropyl Myristate | 8 | 8 | 8 | 8 | 8 |
| Titanium Oxide | 10 | 10 | 10 | 10 | 10 |
| Calcium Carbonate Obtained in Example 1 | 5 | — | — | — | — |
| Calcium Carbonate Obtained in Example 2 | — | 5 | — | — | — |
| Calcium Carbonate Obtained in Comparative Example 1 | — | — | 5 | — | — |
| Calcium Carbonate Obtained in Comparative Example 2 | — | — | — | 5 | — |
| Calcium Carbonate Obtained in Comparative Example 3 | — | — | — | — | 5 |
| Total (g) | 78 | 78 | 78 | 78 | 78 |
| Estimation of Feel | AA | AA | B | B | A |

As clear from the results shown in Table 2, the cosmetics in which the surface-treated spherical calcium carbonate particles having on the surfaces a hydrous silica coating, and further a silicone oil coating on the hydrous silica coating according to the invention are superior in water repellency, and hence are superior in feel.

However, both the cosmetics in which the spherical calcium carbonate particles having only a silicone coating thereon were incorporated and the cosmetics in which the spherical calcium carbonate particles treated with a silane coupling agent in place of a silicone oil were incorporated were found to be inferior in feel. The cosmetics in which the spherical calcium carbonate particles surface-treated with sodium myristate were incorporated were also found to be insufficient in feel.

The invention claimed is:

1. Surface-treated spherical calcium carbonate particles for use in cosmetics, comprising:
spherical calcium carbonate particles having a volume mean diameter in a range from 0.5 to 20 and having on their surfaces a hydrous silica coating in an amount of 1.0-5.0 parts by weight in terms of $SiO_2$ relative to 100 parts by weight of the spherical calcium carbonate particles, and further a silicone oil coating on the hydrous silica coating, in an amount of 1.0-8.0 parts by weight relative to 100 parts by weight of the spherical calcium carbonate particles having on their surfaces the hydrous silica coating.

2. Cosmetics comprising the surface-treated spherical calcium carbonate particles for use in cosmetics according to claim 1.

3. A method for producing surface-treated spherical calcium carbonate particles for use in cosmetics comprising:
adding an aqueous solution of an alkali metal silicate to an aqueous dispersion of spherical calcium carbonate particles having a volume median diameter in a range of 0.5 to 20 µm;
adding an acid to the aqueous dispersion so as to adjust pH thereof to a range from 5.0 to 9.0, thereby separating a resulting product obtained, washing and drying the resulting product so as to obtain spherical calcium carbonate particles having on their surfaces a hydrous silica coating;
kneading the spherical calcium carbonate particles having on their surfaces the hydrous silica coating with a silicone oil together with a volatile organic solvent so as to obtain a kneaded product; and
heating the kneaded product so as to dry and remove the volatile organic solvent therefrom, thereby forming a silicone oil coating on the hydrous silica coating of the spherical calcium carbonate particles.

4. The method according to claim 3, in which the acid is an inorganic acid.

5. The method according to claim 3, in which the kneaded product is heated at a temperature in a range from 110 to 150° C.

6. The method according to claim 3, in which the volatile organic solvent is an aliphatic lower alcohol having from 1 to 4 carbons.

7. Surface-treated spherical calcium carbonate particles for use in cosmetics, comprising:
spherical calcium carbonate particles having a volume mean diameter in a range from 0.5 to 20 µm, and having on their surfaces a hydrous silica coating in an amount of 1.0-5.0 parts by weight in terms of $SiO_2$ relative to 100 parts by weight of the spherical calcium carbonate particles, and further a silicone oil coating in an amount of 1.0-8.0 parts by weight relative to 100 parts by weight of the spherical calcium carbonate particles having on their surfaces the hydrous silica coating, which are obtained by a method comprising:
adding an aqueous solution of an alkali metal silicate to an aqueous dispersion of spherical calcium carbonate particles having a volume median diameter in a range of 0.5 to 20 µm;
adding an acid to the aqueous dispersion so as to adjust pH thereof to a range from 5.0 to 9.0, thereby separating a resulting product obtained, washing and drying the resulting product so as to obtain spherical calcium carbonate particles having on their surfaces a hydrous silica coating;
kneading the spherical calcium carbonate particles having on their surfaces the hydrous silica coating with a silicone oil together with a volatile organic solvent so as to obtain a kneaded product; and
heating the kneaded product so as to dry and remove the volatile organic solvent therefrom, thereby forming a silicone oil coating on the hydrous silica coating of the spherical calcium carbonate particles.

8. Cosmetics comprising the surface-treated spherical calcium carbonate particles for use in cosmetics according to claim 7.

9. The surface-treated spherical calcium carbonate particles for use in cosmetics according to claim 1,
wherein the surface-treated spherical calcium carbonate particles have water repellency in a range of 40 mL or more when expressed with an amount of isopropyl alcohol,
wherein the amount of isopropyl alcohol is a volume of isopropyl alcohol in a water-isopropyl alcohol solution having a total volume of 300 mL at which the water-isopropyl alcohol solution first shows precipitation or turbidity when the amount of isopropyl alcohol in the water-isopropyl alcohol solution is increased by 5 mL from 0 mL and an amount of water is decreased by 5 mL from 300 mL.

10. The surface-treated spherical calcium carbonate particles for use in cosmetics according to claim 1,
wherein the surface-treated spherical calcium carbonate particles have a mean coefficient of friction in a range of 0.70 or smaller.

* * * * *